(12) United States Patent
Orle et al.

(10) Patent No.: US 7,504,217 B2
(45) Date of Patent: Mar. 17, 2009

(54) NS5A NUCLEOTIDE SEQUENCE VARIATION AS A MARKER FOR INTERFERON RESPONSE

(75) Inventors: Karina Anna Orle, Oakland, CA (US); Andrew Michael Ackrill, Hitchin (GB); Morris Paterson, London (GB)

(73) Assignee: Roche Palo Alto LLC, Palo Alto, CA (US)

( * ) Notice: Subject to any disclaimer, the term of this patent is extended or adjusted under 35 U.S.C. 154(b) by 350 days.

(21) Appl. No.: 11/117,667

(22) Filed: Apr. 27, 2005

(65) Prior Publication Data

US 2005/0260567 A1 Nov. 24, 2005

Related U.S. Application Data

(60) Provisional application No. 60/566,274, filed on Apr. 29, 2004.

(51) Int. Cl.
C12Q 1/68 (2006.01)
C12P 19/34 (2006.01)

(52) U.S. Cl. .......................... 435/6; 435/91.2

(58) Field of Classification Search .................. 435/91.1
See application file for complete search history.

(56) References Cited

U.S. PATENT DOCUMENTS

| | | | |
|---|---|---|---|
| 6,030,785 | A | 2/2000 | Katze et al. |
| 6,326,151 | B1 | 12/2001 | Katze et al. |
| 6,433,159 | B1 * | 8/2002 | Anderson ................... 536/24.5 |
| 2005/0069522 | A1 | 3/2005 | Colonno et al. |

FOREIGN PATENT DOCUMENTS

| | | |
|---|---|---|
| WO | WO 97/16204 A1 | 5/1997 |
| WO | WO 97/41883 A1 | 11/1997 |
| WO | WO 00/66141 A2 | 9/2000 |
| WO | WO-03/093492 | 11/2003 |

OTHER PUBLICATIONS

Mackay et al. Nucleic acids research, vol. 30, No. 6, pp. 1292-1305, 2002.*
Ferenci, Peter., Journal of Antimicrobial Chemotherapy, vol. 53, pp. 15-18, Jan. 2004; online Nov. 2003.*
Schiappa et al., The Journal of Infectious Diseases, vol. 185, pp. 868-877, 2002.*
Berg, Thomas, et al., "Mutations in the E2-PePHD and NS5A Region of Hepatitis C Virus Type 1 and the Dynamics of Hepatitis C Viremia Decline During Interferon Alfa Treatment", *Heptatology*, 2000, 32(6): 1386-1395.
Enomoto, Nobuyuki, et al., "Comparison of Full-length Sequences of Interferon-Sensitive and Resistant Hepatitis C Virus I b", *J. Clin. Invest.*, Jul. 1995, 96: 224-230.
Fan, Wenmei, et al., "Nonstructural 5A gene variability of hepatitis C virus (HCV) during a 10-year follow up", *J. Gastroenterol.*, 2005, 40:43-51.

Franguel, Lionel, et al., "Mutations in NS5A Region of Hepatitis C Virus Genome Correlate With Presence of NS5A Antibodies and Response to Interferon Therapy for Most Common European Hepatitis C Virus Genotypes", *Hepatology*, 1998, 28(6): 1674-1679.
Gerotto, Martina, et al., "Effect of Retreatment with Interferon Alone or Interferon plus Ribavirin on Hepatitis C Virus Quasispecies Diversification in Nonresponder Patients with Chronic Hepatitis C", *J. Virol.*, Sep. 1999, 73(9): 7241-7247.
Hofgartner, Wolfgang T., "Mutations in the NS5A Gene of Hepatitis C Virus in North American Patients Infected With HCV Genotype 1a or 1b", *J. Med. Virol.*, 1997, 53:118-126.
Ibarrola, Nieves, et al., "Response to Retreatment With Interferon-a Plus Ribavirin in Chronic Hepatitis C Patients Is Independent of the NS5A Gene Nucleotide Sequence", *Am. J. Gastroenterol.*, 1999, 94(9): 2487-2495.
Kobayashi, Makoto, et al., "Amino Acid Substitutions in the Nonstructural Region 5A of Hepatitis C Virus Genotypes 2a and 2b and Its Relation to Viral Load and Response to Interferon", *Am. J. Gastroenterol.*, 2002, 97(4): 988-998.
McKechnie, Victoria M. et al., "The NS5a Gene of Hepatitis C Virus in Patients Treated With Interferon-a", *J. Med. Virol.*, 2000, 60:367-378.
Murphy, Melissa D., et al., "Analysis of Sequence Configurations of the ISDR, PKR-Binding Domain, and V3 Region as Predictors of Response to Induction Interferon-a and Ribavirin Therapy in Chronic Hepatitis C Infection", *Dig. Dis. Sci.*, Jun. 2002, 47(6): 1195-1205.
Nousbaum, J.-B., et al., "Prospective Characterization of Full-Length Hepatitis C Virus NS5A Quasispecies during Induction and Combination Antiviral Therapy", *J. Virol.*, Oct. 2000, 74(19): 9028-9038.
Odeberg, Jacob, et al., "Variation in the Hepatitis C Virus NS5a Region in Relation to Hypervariable Region 1 Heterogeneity During Interferon Treatment", *J. Med. Virol.*, 1998, 56: 33-38.
Paterson, Morris, et al., "Selection of HCV NS5A Quasispecies During IFN Therapy in Patients with Chronic HCV", *Dig. Dis. Sci.*, Jul. 2001, 46(7): 1399-1408.
Polyak, Stephen J., et al., "Characterization of the Effects of Hepatitis C Virus Nonstructural 5A Protein Expression in Human Cell Lines and on Interferon-Sensitive Virus Replication", *Hepatology*, 1999, 29: 1262-1271.
Polyak, Stephen J., et al., "Evolution of Hepatitis C Virus Quasispecies in Hypervariable Region 1 and the Putative Interferon Sensitivity-Determining Region during Interferon Therapy and Natural Infection", *J. Virol.*, May 1998, 72(5): 4288-4296.
Puig-Basagoiti, Francesc, et al., "Dynamics of hepatitis C virus NS5A quasispecies during interferon and ribavirin therapy in responder and non-responder patients with genotype 1b chronic hepatitis C", *J. Gen. Virol.*, 2005, 86: 1067-1075.
Puig-Basagoiti, Francesc, et al., "Influence of the Genetic Heterogeneity of the ISDR and PePHD Regions of Hepatitis C Virus on the Response to Interferon Therapy in Chronic Hepatitis C", *J. Med. Virol.*, 2001, 65: 35-44.

(Continued)

*Primary Examiner*—Gary Benzion
*Assistant Examiner*—Cynthia B Wilder
(74) *Attorney, Agent, or Firm*—David J. Chang

(57) ABSTRACT

Methods and reagents for determining a nucleotide variation at position 937 of the HCV-1a NS5A gene useful in predicting an individual's response to interferon treatment are presented.

17 Claims, No Drawings

OTHER PUBLICATIONS

Sarrazin, Christoph, et al., "Mutations in the Protein Kinase-Binding Domain of the NS5A Protein in Patients Infected with Hepatitis C Virus Type 1a Are Associated with Treatment Response", *J. Infect. Dis.*, 2000, 181: 432-441.

Schiappa, Deborah A., et al., "Relationship of Hepatitis C Genotype 1 NS5A Sequence Mutations to Early Phase Viral Kinetics and Interferon Effectiveness", *J. Infect. Dis.*, 2002, 185: 868-877.

Witherell, Gary W., et al., "Statistical Analysis of Combined Substitutions in Nonstructural 5A Region of Hepatitis C Virus and Interferon Response", *J. Med. Virol.*, 2001, 63: 8-16.

Zeuzem, Stefan, et al., "Mutations in the Nonstructural 5A Gene of European Hepatitis C Virus Isolates and Response to Interferon Alfa", *Hepatology*, 1997, 25: 740-744.

EMBL /GenBank Database Accession No. AX441173, Sequence 13 from Patent WO0213855, Jun. 28, 2002.

Taguchi, Takashi, et al., "Hepatitis C virus NS5A protein interacts with 2',5'-oligoadenylate synthetase and inhibits antiviral activity iof IFN in an IFN sensitivity-determining region-independent manner", *J. Gen. Virol.*, 2004, 85(4): 959-969.

* cited by examiner

SEQUENCE LISTING

<160> NUMBER OF SEQ ID NOS: 11

<210> SEQ ID NO 1
<211> LENGTH: 1338
<212> TYPE: DNA
<213> ORGANISM: Hepatitis C virus

<400> SEQUENCE: 1

```
tcctggctaa gggacatctg ggactggata tgcgaggtgc tgagcgactt taagacctgg      60
ctgaaagcca agctcatgcc acaactgcct gggattccct ttgtgtcctg ccagcgcggg     120 tataggggg  tctggcgagg agacggcatt atgcacactc gctgccactg tggagctgag     180
```

```
atcactggac atgtcaaaaa cgggacgatg aggatcgtcg gtcctaggac ctgcaagaac    240
atgtggagtg ggacgttctt cattaatgcc tacaccacgg cccctgtac tcccttcct    300 gcgccgaact ataagttcgc gctgtggagg gtgtctgcag aggaatacgt ggagataagg    360
cgggtggggg acttccacta cgtatcgggc atgactactg acaatctcaa atgcccgtgc    420
cagatcccat cgcccgaatt tttcacagaa ttggacgggg tgcgcctaca taggtttgcg    480 ccccccttgca agcccttgct gcgggaggag gtatcattca gagtaggact ccacgagtac    540
ccggtggggg cgcaattacc ttgcgagccc gaaccggacg tagccgtgtt gacgtccatg    600
ctcactgatc cctcccatat aacagcagag gcggccggga aaggttggc gagagggtca    660 ccccccttcta tggccagctc ctcggctagc cagctgtccg ctccatctct caaggcaact    720
tgcaccgcca accatgactc ccctgacgcc gagctcatag aggctaacct cctgtggagg    780
caggagatgg gcggcaacat caccagggtt gagtcagaga acaaagtggt gattctggac    840
tccttcgatc cgcttgtggc agaggaggat gagcgggagg tctccgtacc cgcagaaatt    900
ctgcggaagt ctcggagatt cgccccagcc ctgcccgtct gggcgcggcc ggactacaac    960
cccctgctag tagagacgtg gaaaaagcct gactacgaac cacctgtggt ccatggctgc    1020
ccgctaccac ctccacggtc ccctcctgtg cctccgcctc ggaaaaagcg tacggtggtc    1080
ctcaccgaat caaccctacc tactgccttg gccgagcttg ccaccaaaag ttttggcagc    1140
tcctcaactt ccggcattac gggcgacaat acgacaacat cctctgagcc cgccccttct    1200
ggctgccccc ccgactccga cgttgagtcc tattcttcca tgccccccct ggaggggag    1260 cctggggatc cggatctcag cgacgggtca tggtcgacgg tcagtagtgg ggccgacacg    1320
gaagatgtcg tgtgctgc                                                  1338
```

<210> SEQ ID NO 2
<211> LENGTH: 446
<212> TYPE: PRT
<213> ORGANISM: Hepatitis C virus

<400> SEQUENCE: 2

```
Ser Trp Leu Arg Asp Ile Trp Asp Trp Ile Cys Glu Val Leu Ser Asp
1               5                   10                  15

Phe Lys Thr Trp Leu Lys Ala Lys Leu Met Pro Gln Leu Pro Gly Ile
            20                  25                  30

Pro Phe Val Ser Cys Gln Arg Gly Tyr Arg Gly Val Trp Arg Gly Asp
        35                  40                  45

Gly Ile Met His Thr Arg Cys His Cys Gly Ala Glu Ile Thr Gly His
    50                  55                  60

Val Lys Asn Gly Thr Met Arg Ile Val Gly Pro Arg Thr Cys Lys Asn
65                  70                  75                  80

Met Trp Ser Gly Thr Phe Phe Ile Asn Ala Tyr Thr Thr Gly Pro Cys
                85                  90                  95

Thr Pro Leu Pro Ala Pro Asn Tyr Lys Phe Ala Leu Trp Arg Val Ser
            100                 105                 110

Ala Glu Glu Tyr Val Glu Ile Arg Arg Val Gly Asp Phe His Tyr Val
        115                 120                 125

Ser Gly Met Thr Thr Asp Asn Leu Lys Cys Pro Cys Gln Ile Pro Ser
    130                 135                 140

Pro Glu Phe Phe Thr Glu Leu Asp Gly Val Arg Leu His Arg Phe Ala
145                 150                 155                 160
```

```
Pro Pro Cys Lys Pro Leu Leu Arg Glu Glu Val Ser Phe Arg Val Gly
            165                 170                 175
Leu His Glu Tyr Pro Val Gly Ser Gln Leu Pro Cys Glu Pro Glu Pro
            180                 185                 190
Asp Val Ala Val Leu Thr Ser Met Leu Thr Asp Pro Ser His Ile Thr
        195                 200                 205
Ala Glu Ala Ala Gly Arg Arg Leu Ala Arg Gly Ser Pro Pro Ser Met
    210                 215                 220
Ala Ser Ser Ser Ala Ser Gln Leu Ser Ala Pro Ser Leu Lys Ala Thr
225                 230                 235                 240
Cys Thr Ala Asn His Asp Ser Pro Asp Ala Glu Leu Ile Glu Ala Asn
                245                 250                 255
Leu Leu Trp Arg Gln Glu Met Gly Gly Asn Ile Thr Arg Val Glu Ser
            260                 265                 270
Glu Asn Lys Val Val Ile Leu Asp Ser Phe Asp Pro Leu Val Ala Glu
        275                 280                 285
Glu Asp Glu Arg Glu Val Ser Val Pro Ala Glu Ile Leu Arg Lys Ser
    290                 295                 300
Arg Arg Phe Ala Pro Ala Leu Pro Val Trp Ala Arg Pro Asp Tyr Asn
305                 310                 315                 320
Pro Leu Leu Val Glu Thr Trp Lys Lys Pro Asp Tyr Glu Pro Pro Val
                325                 330                 335
Val His Gly Cys Pro Leu Pro Pro Arg Ser Pro Val Pro Pro
            340                 345                 350
Pro Arg Lys Lys Arg Thr Val Val Leu Thr Glu Ser Thr Leu Pro Thr
            355                 360                 365
Ala Leu Ala Glu Leu Ala Thr Lys Ser Phe Gly Ser Ser Ser Thr Ser
        370                 375                 380
Gly Ile Thr Gly Asp Asn Thr Thr Thr Ser Ser Glu Pro Ala Pro Ser
385                 390                 395                 400
Gly Cys Pro Pro Asp Ser Asp Val Gly Ser Tyr Ser Ser Met Pro Pro
                405                 410                 415
Leu Glu Gly Glu Pro Gly Asp Pro Asp Leu Ser Asp Gly Ser Trp Ser
            420                 425                 430
Thr Val Ser Ser Gly Ala Asp Thr Glu Asp Val Val Cys Cys
        435                 440                 445

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 3
gattcgcccc agccctgccc a                                             21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 4
ggccaaggca gtaggtaggg t                                             21
```

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
gtagtccggc cgccgcgccc agac                                              24

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
cataggtttg cgcccccttg c                                                 21

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (5)
<223> OTHER INFORMATION: where y is c or t/u

<400> SEQUENCE: 7
cagaygggca gggctggggc ga                                                22

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 8
gagatgggca ccatcacc                                                     18

<210> SEQ ID NO 9
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 9
ggccaaagta ggtagggt                                                     18

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Probe

<400> SEQUENCE: 10
agtctcggag attcgcccc                                                    19

<210> SEQ ID NO 11
<211> LENGTH: 14
<212> TYPE: DNA

-continued

```
<213> ORGANISM: Artificial Sequence
<220> FEATURE:
<223> OTHER INFORMATION: Description of Artificial Sequence: Probe
<220> FEATURE:
<221> NAME/KEY: misc_feature
<222> LOCATION: (10)
<223> OTHER INFORMATION: where r is a or g

<400> SEQUENCE: 11
gccctgcccr tctg                                                          14
```

NS5A NUCLEOTIDE SEQUENCE VARIATION AS A MARKER FOR INTERFERON RESPONSE

CROSS REFERENCE TO RELATED INVENTIONS

This application claims the priority benefit under Title 35 U.S.C. 119(e) of U.S. Provisional Application 60/566,274, filed Apr. 29, 2004, the disclosure of which is herein incorporated by reference in its entirety.

BACKGROUND OF THE INVENTION

Hepatitis C virus (HCV) infection is an important clinical problem worldwide. In the United States alone, an estimated four million individuals are chronically infected with HCV. HCV, the major etiologic agent of non-A, non-B hepatitis, is transmitted primarily by transfusion of infected blood and blood products (Cuthbert et al., 1994, Clin. Microbiol Rev. 7:505-532). Prior to the introduction of anti-HCV screening in mid-1990, HCV accounted for 80-90% of posttransfusion hepatitis cases in the United States. A high rate of HCV infection is also seen in individuals with bleeding disorders or chronic renal failure, groups that have frequent exposure to blood and blood products.

Acute infection with HCV results in persistent viral replication and progression to chronic hepatitis in approximately 90% of cases. For many patients, chronic HCV infection results in progressive liver damage and the development of cirrhosis. In patients with an aggressive infection, cirrhosis can develop in as little as two years, although a time span of 10-20 years is more typical. In 30-50% of chronic HCV patients, liver damage may progress to the development of hepatocellular carcinoma. In general, hepatocellular carcinoma is a late occurrence and may take greater than 30 years to develop (Bisceglie et al., 1995, Semin. Liver Dis. 15:64-69). The relative contribution of viral or host factors in determining disease progression is not clear.

HCV is an enveloped virus containing a positive-sense single-stranded RNA genome of approximately 9.5 kb. On the basis of its genome organization and virion properties, HCV has been classified as a separate genus in the family Flaviviridae, a family that also includes pestiviruses and flaviviruses (Alter, 1995, Semin. Liver Dis. 15:5-14). The viral genome consists of a lengthy 5' untranslated region (UTR), a long open reading frame encoding a polyprotein precursor of approximately 3011 amino acids, and a short 3' UTR. The polyprotein precursor is cleaved by both host and viral proteases to yield mature viral structural and nonstructural proteins. HCV encodes two proteinases, a zinc-dependent metalloproteinase, encoded by the NS2-NS3 region, and a serine proteinase encoded in the NS3/NS4 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4B, and that of NS5A (the amino- terminal half of nonstructural protein 5) remain unknown.

Interferon-alpha (interferon) is a Food and Drug Administration-approved treatment for chronic HCV infection. The effects of interferon are mediated through different cellular inducible proteins, including double-stranded RNA-activated protein kinase (PKR) (Gale et al., 1997, Virology 230:217-227). Only 8 to 12% of patients with HCV genotype 1 have a sustained clinical virological response to interferon therapy (Carithers et al., 1997, Hepatology 26:83S-88S; Lindsay, 1997, Hepatology 26:71S-77S). Recently, combination therapy with interferon and the guanosine analogue, ribavirin, was shown to be superior to interferon monotherapy in producing sustained biochemical and virological responses (Poynard et al., 1998, Lancet 352:1426-1432). However, despite the significant improvement in rates of sustained response, as many as 60% of patients with high-titer HCV genotype 1 infection are nonresponsive to combination therapy. For example, the response rate in patients infected with HCV-1b is less than 40%. Similar low response rates for patients infected with prototype United States genotype, HCV-1a, have also been reported (Mahaney et al. 1994, Hepatology 20:1405-1411). In contrast, the response rate of patients infected with HCV genotype-2 is nearly 80% (Fried et al., 1995, Semin. Liver Dis. 15:82-91.) Expression of the entire HCV polyprotein has been shown to inhibit interferon-induced signaling in human U2-OS osteosarcoma cells (Heim et al., 1999, J. Virol. 73:8469-8475). It was not reported which HCV protein was responsible for this effect. The relationship between interferon-response and the nonstructural 5A (NS5A) sequence of HCV is controversial. Response to interferon therapy differs among the HCV subtypes, with the HCV-1b subtype being particularly resistant to interferon treatment (Alter et al., 1998, MMWR Recomm. Rep. 47 (RR-19):1-39). A comparison of the full length HCV nucleic acid sequence from interferon-resistant and interferon-sensitive viruses from HCV infected patients revealed missense substitutions corresponding to the carboxy terminus of NS5A (Enomoto et al., 1995, J. Clin. Invest. 96:224-230). The corresponding 40 amino acid region of NS5A (amino acids 2209-2248 of the HCV polyprotein) has been termed the interferon sensitivity determining region, or ISDR (Enomoto et al., 1995). The ISDR is enclosed within a region in the NS5A protein which can bind to and inhibit the function of PKR (Gale et al., Mol. Cell Biol., 1998, 18:5208-5218). Enomoto et al. (1996, N. Eng. J. Med. 334:77-81) proposed a model in which patients who respond to interferon-therapy are infected by viruses with multiple substitutions in the ISDR (compared to the interferon-resistant HCV 1b-J prototype sequence) whereas patients who fail interferon-therapy are infected by viruses with few substitutions in the ISDR.

Of the 25 studies that have published ISDR sequences from interferon-resistant and interferon-sensitive viruses, nine support the Enomoto model and conclude that, at the 5% significance level, the data provide sufficient evidence that interferon-response and substitutions in the ISDR are dependent (Enomoto et al., 1995, 1996; Chayama et al., 1997, Hepatology, 25:745-749; Kurosaki et al., 1997, Hepatology 25:750-753; Fukuda et al., 1998, J. Gastroenterol. Hepatol. 13:412-418; Saiz et al., 1998, J. Infect. Dis. 177:839-847; Murashima et al., 1999, Scand. J. Infect. Dis. 31:27-32; Sarrazin et al. 1999, J. Hepatol. 30:1004-1013; Sakuma et al., 1999, J. Infect. Dis. 180:1001-1009). The other 16 studies were unable to conclude that there is a correlation (Hofgartner et al., 1997, J. Med. Virol. 53:118-126; Khorsi et al., 1997, J. Hepatol. 27:72-77; Squadrito et al., 1997, Gastroenterology 113:567-572; Zeuzem et al., 1997, Hepatology 25:740-744; Duverlie et al., 1998, J. Gen. Virol. 79:1373-1381; Franguel et al., 1998, Hepatology 28:1674-1679; Odeberg et al., 1998, J. Med. Virol. 56:33-38; Pawlotsky et al., 1998, J. Virol. 72:2795-2805; Polyak et al., 1998, J. Virol. 72:4288-4296; Rispeter et al., 1998, J. Hepatol. 29:352-361; Chung et al., 1999, J. Med. Virol. 58:353-358; Sarrazin et al. 1999, J. Hepatol. 30:1004-1013; Squadrito et al., 1999, J. Hepatol. 30:1023-1027; Ibarrola et al., 1999, Am. J. Gastroenterol. 94:2487-2495; Mihm et al., 1999, J. Med. Virol. 58:227-234; Arase et al., 1999, Intern. Med. 38:461-466). Interestingly, seven of the nine studies that support a correlation are based on HCV isolates from Japan whereas 15 of the 16 studies that do not support a correlation are based on isolates from European and North American isolates. Although a statistically significant correlation between interferon response and ISDR sequence in North American and European studies are generally not found, there is evidence that a relationship does exist. When the intermediate and mutant classes of ISDR sequences from an individual study are combined, the response rates to interferon are higher than those in patients with the wild-type class of ISDR sequence (Herion and Hoofnagle, 1997, *Hepatology* 25:769-771).

SUMMARY OF THE INVENTION

The present invention is based on the discovery that in human subjects infected with the HCV-1a subtype, there is a significant association between nucleotide sequence substitutions at position 937 of the HCV NS5A gene and the infected individual's response to treatment by interferon. Specifically, individuals infected with a virus which contains a "G" at position 937 of the NS5A gene which results in the presence of valine at position 313 of the NS5A protein, will have an increased likelihood of sustained virologic response to interferon treatment. Conversely, individuals infected with a virus which contains an "A" at position 937 of the NS5A gene which results in the presence of isoleucine at position 313 of the NS5A protein, will have an increased likelihood of virologic non-response to interferon treatment. To our knowledge, this marks the first time a specific nucleotide and amino acid mutation has been associated with response to interferon treatment. Furthermore, the position of this particular mutation is not in the ISDR or in the PKR-binding region of the NS5A protein.

Accordingly, the present invention provides for methods for predicting the response of a human subject infected with HCV-1a to interferon treatment. In one embodiment, the method comprises providing an HCV-1a polynucleotide from the human subject comprising a portion that includes nucleotide position 937 of the NS5A gene, and determining whether the nucleotide at position 937 is "G" or not, where the presence of a "G" at position 937 indicates an increased likelihood of sustained virologic response to interferon treatment by the human subject. In another embodiment, the method comprises providing an HCV-1a polypeptide from the human subject comprising a portion that includes amino acid position 313 of the NS5A protein, and determining whether the amino acid at position 313 is valine or not, where the presence of valine at position 313 indicates an increased likelihood of sustained virologic response to interferon treatment by the human subject.

The present invention also provides for methods for treating a human subject infected with HCV. In one embodiment, the method comprises providing an HCV-1a polynucleotide from the human subject comprising a portion that includes nucleotide position 937 of the NS5A gene, determining whether the nucleotide at position 937 is "G" or not, and if the nucleotide at position 937 is "G", treating the human subject with interferon. In another embodiment, the method comprises providing an HCV-1a polypeptide from the human subject comprising a portion that includes amino acid position 313 of the NS5A protein, and determining whether the amino acid at position 313 is valine or not, and if the amino acid at position 313 is valine, treating the human subject with interferon.

The present invention also provides for an oligonucleotide that can be used to detect a nucleotide substitution at position 937 in the NS5A gene of HCV-1a. In preferred embodiments, the oligonucleotide is between 14 and 35 nucleotides in length and is essentially complementary to either strand in a region of the NS5A gene that includes position 937. The present invention further provides for a kit which is useful for predicting response to interferon by a human subject infected with HCV-1a. Specifically, the kit comprises an oligonucleotide that can be used to detect a nucleotide substitution at position 937 in the NS5A gene of HCV-1a, wherein the oligonucleotide is between 14 and 35 nucleotides in length and is essentially complimentary to either strand in a region of the NS5A gene that includes position 937, and a polymerase. The foregoing and other advantages and features of the invention, and the manner in which the same are accomplished, will become more readily apparent upon consideration of the following detailed description of the invention taken in conjunction with the accompanying examples, which illustrate exemplary embodiments.

DETAILED DESCRIPTION OF THE INVENTION

Definitions

The phrase "nucleotide at position 937 of the NS5A gene" means the locus at nucleotide position 937 of the HCV-1a NS5A cDNA or RNA with the sequence shown in SEQ ID NO:1 as a reference sequence for alignment, wherein SEQ ID NO:1 represents the NS5A encoding region between nucleotide position 6264 and nucleotide position 7601 of the HCV-1a genome nucleotide sequence from GenBank Accession Number M67463.

The phrase "amino acid at position 313 of the NS5A protein" means the amino acid at position 313 of the HCV-1a NS5A protein with the sequence shown in SEQ ID NO:2 as a reference sequence for alignment wherein SEQ ID NO:2 represents the polypeptide sequence of the NS5A protein which spans from amino acid position 1975 to amino acid position 2420 of the HCV-1a genome polyprotein from GenBank Accession Number P26662.

The terms "nucleotide substitution(s)" and "nucleotide variation(s) are herein used interchangeably and refer to nucleotide change(s) at a position in a reference nucleotide sequence of a particular gene.

The terms "amino acid mutation" and "amino acid substitution" are herein used interchangeably to refer to an amino acid change at a position in a reference protein sequence which results from a nucleotide substitution or variation in the reference nucleotide sequence encoding the reference protein.

The term "genotyping" means determining the nucleotide(s) at a particular gene locus.

The term "response" to treatment with interferon is a desirable response to the administration of an agent. The terms "Sustained Virologic Response" and "Complete Response" to treatment with interferon are herein used interchangeably and refer to the absence of detectable HCV RNA in the sample of an infected subject by RT-PCR both at the end of treatment and twenty-four weeks after the end of treatment. The terms "Virologic Non-Response" and "No Response" to treatment with interferon are herein used interchageably and refer to the presence of detectable HCV RNA in the sample of an infected subject by RT-PCR throughout treatment and at the end of treatment.

The terms "sample" or "biological sample" refers to a sample of tissue or fluid isolated from an individual, including, but not limited to, for example, tissue biopsy, plasma, serum, whole blood, spinal fluid, lymph fluid, the external sections of the skin, respiratory, intestinal and genitourinary tracts, tears, saliva, milk, blood cells, tumors, organs. Also included are samples of in vitro cell culture constituents (including, but not limited to, conditioned medium resulting from the growth of cells in culture medium, putatively virally infected cells, recombinant cells, and cell components).

The terms "interferon" and "interferon-alpha" are used herein interchangeably and refer to the family of highly homologous species-specific proteins that inhibit viral replication and cellular proliferation and modulate immune response. Typical suitable interferons include, but are not limited to, recombinant interferon alpha-2b such as Intron® A interferon available from Schering Corporation, Kenilworth, N.J., recombinant interferon alpha-2a such as Roferon®-A interferon available from Hoffmann-La Roche, Nutley, N.J., recombinant interferon alpha-2C such as Berofor® alpha 2 interferon available from Boehringer Ingelheim Pharmaceutical, Inc., Ridgefield, Conn., interferon alpha-n1, a purified blend of natural alpha interferons such as Sumiferon® available from Sumitomo, Japan or as Wellferon® interferon alpha-n1 (INS) available from the Glaxo-Wellcome Ltd., London, Great Britain, or a consensus alpha interferon such as those described in U.S. Pat. Nos. 4,897,471 and 4,695,623 (especially Examples 7, 8 or 9 thereof) and the specific product available from Amgen, Inc., Newbury Park, Calif., or interferon alpha-n3 a mixture of natural alpha interferons made by Interferon Sciences and available from the Purdue Frederick Co., Norwalk, Conn., under the Alferon Tradename. The use of interferon alpha-2a or alpha-2b is preferred.

The term "pegylated interferon alpha" as used herein means polyethylene glycol modified conjugates of interferon alpha, preferably interferon alpha-2a and alpha-2b. Typical suitable pegylated interferon alpha include, but are not limited to, Pegasys® (peginterferon alpha-2a) and Peg-Intron® (peginterferon alpha-2b).

As used herein, the terms "nucleic acid," "nucleotide," "polynucleotide" and "oligonucleotide" refer to primers, probes, oligomer fragments to be detected, oligomer controls and unlabeled blocking oligomers and shall be generic to polydeoxyribonucleotides (containing 2-deoxy-D-ribose), to polyribonucleotides (containing D-ribose), and to any other type of polynucleotide which is an N-glycoside of a purine or pyrimidine base, or modified purine or pyrimidine bases.

A nucleic acid, nucleotide, polynucleotide or oligonucleotide can comprise phosphodiester linkages or modified linkages such as phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone linkages, and combinations of such linkages.

A nucleic acid, nucleotide, polynucleotide or oligonucleotide can comprise the five biologically occurring bases (adenine, guanine, thymine, cytosine and uracil) and/or bases other than the five biologically occurring bases. For example, a polynucleotide of the invention might contain at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxymethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, 3-(3-amino-3-N-2-carboxypropyl) uracil, (acp3)w, 2,6-diaminopurine, and 5-propynyl pyrimidine.

Furthermore, a nucleic acid, nucleotide, polynucleotide or oligonucleotide can comprise one or more modified sugar moieties such as arabinose, 2-fluoroarabinose, xylulose, and hexose.

It is not intended that the present invention be limited by the source of a nucleic acid, nucleotide, polynucleotide or oligonucleotide. A nucleic acid, nucleotide, polynucleotide or oligonucleotide can be from a human or non-human mammal, or any other organism, or derived from any recombinant source, synthesized in vitro or by chemical synthesis. A nucleic acid, nucleotide, polynucleotide or oligonucleotide may be DNA, RNA, cDNA, DNA-RNA, locked nucleic acid (LNA), peptide nucleic acid (PNA), a hybrid or any mixture of the same, and may exist in a double-stranded, single-stranded or partially double-stranded form. The nucleic acids of the invention include both nucleic acids and fragments thereof, in purified or unpurified forms, including genes, chromosomes, plasmids, the genomes of biological material such as microorganisms, e.g., bacteria, yeasts, viruses, viroids, molds, fungi, plants, animals, humans, and the like.

There is no intended distinction in length between the terms nucleic acid, nucleotide, polynucleotide and oligonucleotide, and these terms will be used interchangeably. These terms include double- and single-stranded DNA, as well as double- and single-stranded RNA.

"Corresponding" means identical to or complementary to a designated sequence.

Because mononucleotides can be reacted to make oligonucleotides in a manner such that the 5' phosphate of one mononucleotide pentose ring is attached to the 3' oxygen of its neighbor in one direction via a phosphodiester linkage, an end of an oligonucleotide is referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide, also may be said to have 5' and 3' ends.

When two different, non-overlapping oligonucleotides anneal to different regions of the same linear complementary nucleic acid sequence, and the 3' end of one oligonucleotide points toward the 5' end of the other, the former may be called the "upstream" oligonucleotide and the latter the "downstream" oligonucleotide.

The term "primer" may refer to more than one primer or a mixture of primers and refers to an oligonucleotide, whether occurring naturally, as in a purified restriction digest, or produced synthetically, which is capable of acting as a point of initiation of polynucleotide synthesis along a complementary strand when placed under conditions in which synthesis of a primer extension product which is complementary to a nucleic acid strand is catalyzed. Such conditions typically include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.), and at a suitable temperature. The primer is preferably single-stranded for maximum efficiency in amplification.

The complement of a nucleic acid sequence as used herein refers to an oligonucleotide which, when aligned with the nucleic acid sequence such that the 5' end of one sequence is paired with the 3' end of the other, is in "antiparallel association." Certain bases not commonly found in natural nucleic acids may be included in the nucleic acids of the present invention and include, for example, inosine, 7-deazaguanine and those discussed above. Complementarity need not be perfect; stable duplexes may contain mismatched base pairs or unmatched bases. Those skilled in the art of nucleic acid technology can determine duplex stability by empirically considering a number of variables including, for example, the length of the oligonucleotide, base composition and sequence of the oligonucleotide, ionic strength, and incidence of mismatched base pairs.

As used herein, the term "probe" refers to an oligonucleotide which can form a duplex structure with a region of a nucleic acid, due to complementarity of at least one sequence in the probe with a sequence in the region and is capable of being detected. The probe, preferably, does not contain a sequence complementary to sequence(s) of a primer in a 5' nuclease reaction. As discussed below, the probe can be labeled or unlabeled. The 3' terminus of the probe can be "blocked" to prohibit incorporation of the probe into a primer extension product. "Blocking" can be achieved by using non-complementary bases or by adding a chemical moiety such as biotin or a phosphate group to the 3' hydroxyl of the last nucleotide, which may, depending upon the selected moiety, serve a dual purpose by also acting as a label for subsequent detection or capture of the nucleic acid attached to the label. Blocking can also be achieved by removing the 3'-OH or by using a nucleotide that lacks a 3'-OH such as a dideoxynucleotide.

The term "label" as used herein refers to any atom or molecule which can be used to provide a detectable (optionally quantifiable) signal, and which can be attached to a nucleic acid or protein. Labels may provide signals detectable by fluorescence, radioactivity, colorimetry, gravimetry, X-ray diffraction or absorption, magnetism, enzymatic activity, and the like. Convenient labels for the present invention include those that facilitate detection of the size of an oligonucleotide fragment.

In certain embodiments of the invention, a "label" is a fluorescent dye. Fluorescent labels may include dyes that are negatively charged, such as dyes of the fluorescein family, or dyes that are neutral in charge, such as dyes of the rhodamine family, or dyes that are positively charged, such as dyes of the cyanine family. Dyes of the fluorescein family include, e.g., FAM, HEX, TET, JOE, NAN and ZOE. Dyes of the rhodamine family include Texas Red, ROX, R110, R6G, and TAMRA. FAM, HEX, TET, JOE, NAN, ZOE, ROX, R110, R6G, and TAMRA are marketed by Perkin-Elmer (Foster City, Calif.), and Texas Red is marketed by Molecular Probes, Inc. (Eugene, Oreg.). Dyes of the cyanine family include Cy2, Cy3, Cy5, and Cy7 and are marketed by Amersham (Amersham Place, Little Chalfont, Buckinghamshire, England).

The term "quencher" as used herein refers to a chemical moiety that absorbs energy emitted from a fluorescent dye, for example, when both the quencher and fluorescent dye are linked to a common polynucleotide. A quencher may re-emit the energy absorbed from a fluorescent dye in a signal characteristic for that quencher and thus a quencher can also be a "label." This phenomenon is generally known as fluorescent resonance energy transfer or FRET. Alternatively, a quencher may dissipate the energy absorbed from a fluorescent dye as heat. Molecules commonly used in FRET include, for example, fluorescein, FAM, JOE, rhodamine, R6G, TAMRA, ROX, DABCYL, and EDANS. Whether a fluorescent dye is a label or an quencher is defined by its excitation and emission spectra, and the fluorescent dye with which it is paired. For example, FAM is most efficiently excited by light with a wavelength of 488 nm, and emits light with a spectrum of 500 to 650 nm, and an emission maximum of 525 nm. FAM is a suitable donor label for use with, e.g., with TAMRA as a quencher which has at its excitation maximum 514 nm. Exemplary non-fluorescent quenchers that dissipate energy absorbed from a fluorescent dye include the Black Hole Quenchers™ marketed by Biosearch Technologies, Inc. (Novato, Calif.).

As defined herein, "5' to 3' nuclease activity". refers to that activity of a template-specific nucleic acid polymerase including either a 5' to 3' exonuclease activity traditionally associated with some DNA polymerases whereby nucleotides are removed from the 5' end of an oligonucleotide in a sequential manner, (e.g., *E. coli* DNA polymerase I has this activity whereas the Klenow fragment does not), or a 5' to 3' endonuclease activity wherein cleavage occurs more than one phosphodiester bond (nucleotide) from the 5' end, or both. Although not intending to be bound by any particular theory of operation, the preferred substrate for 5' to 3' endonuclease activity-dependent cleavage on a probe-template hybridization complex is a displaced single-stranded nucleic acid, a fork-like structure, with hydrolysis occurring at the phosphodiester bond joining the displaced region with the base-paired portion of the strand, as discussed in Holland et al., 1991, *Proc. Natl. Acad. Sci. USA* 88:7276-80, hereby incorporated by reference in its entirety.

The term "adjacent" as used herein refers to the positioning of the primer with respect to the probe on its complementary strand of the template nucleic acid. The primer and probe may be separated by more than 20 nucleotides, by 1 to about 20 nucleotides, more preferably, about 1 to 10 nucleotides, or may directly abut one another, as may be desirable for a detection with a polymerization-independent process. Alternatively, for use in the polymerization-dependent process, as when the present method is used in a PCR amplification and detection methods as taught herein, the "adjacency" may be anywhere within the sequence to be amplified, anywhere downstream of a primer such that primer extension will position the polymerase so that cleavage of the probe occurs.

As used herein, the term "thermostable nucleic acid polymerase" refers to an enzyme which is relatively stable to heat when compared, for example, to nucleotide polymerases from *E. coli* and which catalyzes the polymerization of nucleoside triphosphates. Generally, the enzyme will initiate synthesis at the 3'-end of the primer annealed to the target sequence, and will continue synthesis of a new strand toward the 5'-end of the template, and if possessing a 5' to 3' nuclease activity, hydrolyzing intervening, annealed probe to release both labeled and unlabeled probe fragments, until synthesis terminates or probe fragments melt off the target sequence. A representative thermostable enzyme isolated from *Thermus aquaticus* (Taq) is described in U.S. Pat. No. 4,889,818 and a method for using it in conventional PCR is described in Saiki et al., 1988, *Science* 239:487-91.

Taq DNA polymerase has a DNA synthesis-dependent, strand replacement 5'-3' exonuclease activity. See Gelfand, "Taq DNA Polymerase" in *PCR Technology Principles and Applications for DNA Amplification*, Erlich, Ed., Stockton Press, N.Y. (1989), Chapter 2. In solution, there is little, if any, degradation of probes.

The term "5' nuclease reaction" of a nucleic acid, primer and probe refers to the degradation of a probe hybridized to the nucleic acid when the primer is extended by a nucleic acid polymerase having 5' to 3' nuclease activity, as described in detail below. Such reactions are based on those described in U.S. Pat. Nos. 6,214,979, 5,804,375, 5,487,972 and 5,210,015, which are hereby incorporated by reference in their entireties.

The term "target nucleic acid" refers to a nucleic acid which can hybridize with a primer and probe in a 5' nuclease reaction and contains one or more nucleotide variation sites.

The terms "stringent" or "stringent conditions", as used herein, denote hybridization conditions of low ionic strength and high temperature, as is well known in the art. See, e.g., Sambrook et al., 2001, *Molecular Cloning: A Laboratory Manual, Third Edition*, Cold Spring Harbor Laboratory Press, Cold Spring Harbor, N.Y.; *Current Protocols in Molecular Biology* (Ausubel et al., ed., J. Wiley & Sons Inc., New York, 1988); Tijssen, 1993, "Overview of principles of hybridization and the strategy of nucleic acid assays" in *Laboratory techniques in biochemistry and molecular biology: Hybridization with nucleic acid probes* (Elsevier), each of which is hereby incorporated by reference. Generally, stringent conditions are selected to be about 5-30° C. lower than the thermal melting point ($T_m$) for the specified sequence at a defined ionic strength and pH. Alternatively, stringent conditions are selected to be about 5-15° C. lower than the $T_m$ for the specified sequence at a defined ionic strength and pH. The $T_m$ is the temperature (under defined ionic strength, pH and nucleic acid concentration) at which 50% of the probes complementary to the target hybridize to the target sequence at equilibrium (as the target sequences are present in excess, at $T_m$, 50% of the probes are occupied at equilibrium). For example, stringent hybridization conditions will be those in which the salt concentration is less than about 1.0 M sodium (or other salts) ion, typically about 0.01 to about 1 M sodium ion concentration at about pH 7.0 to about pH 8.3 and the temperature is at least about 25° C. for short probes (e.g., 10 to 50 nucleotides) and at least about 55° C. for long probes (e.g., greater than 50 nucleotides). Stringent conditions may also be modified with the addition of hybridization destabilizing agents such as formamide. An exemplary non-stringent or low stringency condition for a long probe (e.g., greater than 50 nucleotides) would comprise a buffer of 20 mM Tris, pH 8.5, 50 mM KCl, and 2 mM $MgCl_2$, and a reaction temperature of 25° C.

The practice of the present invention will employ, unless otherwise indicated, conventional techniques of molecular biology, microbiology and recombinant DNA techniques, which are within the skill of the art. Such techniques are explained fully in the literature. See, e.g., Sambrook et al., 2001, *Molecular Cloning: A Laboratory Manual, Third Edition*, Cold Spring Harbor Laboratory Press, Cold Spring Harbor, N.Y.; Oligonucleotide Synthesis (M. J. Gait, ed., 1984); *Nucleic Acid Hybridization* (B. D. Hames & S. J. Higgins, eds., 1984); *A Practical Guide to Molecular Cloning* (B. Perbal, 1984); and a series, *Methods in Enzymology* (Academic Press, Inc.).

Nucleotide Sequence of HCV-1a NS5A Gene

The nucleotide sequence of the entire HCV-1a genome is available from GenBank under accession number M67463 and the NS5A-encoding region between nucleotide position 6264 and position 7601 is provided as SEQ ID NO:1. The newly discovered single nucleotide substitution occurs at position 937. The G937A substitution corresponds to a change in the encoded amino acid from Valine to Isoleucine.

Genotyping Methods

Numerous techniques for detecting nucleotide or amino acid variations are known in the art and can all be used to practise the methods of the present invention. The particular method used to identify the sequence variation is not a critical aspect of the invention. Although considerations of performance, cost, and convenience will make particular methods more desirable than others, it will be clear that any method that can identify the nucleotide at position 937 of SEQ ID NO:1 or the amino acid at position 313 of SEQ ID NO:2 will provide the information needed to practise the invention. The techniques can be polynucleotide-based or protein-based. In either case, the techniques used must be sufficiently sensitive so as to accurately detect single nucleotide or amino acid variations.

In a polynucleotide-based detection method, genotyping is accomplished by identifying the nucleotide present at the substitution site, nucleotide position 937 of SEQ ID NO: 1. Any type of biological sample from a HCV-1a-infected individual containing HCV-1a polynucleotide may be used for determining the genotype. Genotyping may be carried out by isolating HCV RNA using standard RNA extraction methods well known in the art. Amplification of RNA can be carried out by first reverse-transcribing the target RNA using, for example, a viral reverse transcriptase, and then amplifying the resulting cDNA, or using a combined high-temperature reverse-transcription-polymerase chain reaction (RT-PCR), as described in U.S. Pat. Nos. 5,310,652; 5,322,770; 5,561,058; 5,641,864; and 5,693,517; each incorporated herein by reference (see also Myers and Sigua, 1995, in *PCR Strategies*, supra, chapter 5). A number of methods are known in the art for identifying the nucleotide present at a single nucleotide position.

The nucleotide at position 937 can be identified by DNA sequencing methods, such as the chain termination method (Sanger et al., 1977, *Proc. Natl. Acad. Sci.* 74:5463-5467, incorporated herein by reference), which are well known in the art. In one embodiment, a subsequence of the gene encompassing the substitution site is amplified and either cloned into a suitable plasmid and then sequenced, or sequenced directly. PCR-based sequencing is described in U.S. Pat. No. 5,075,216; Brow, in *PCR Protocols,* 1990, (Innis et al., eds., Academic Press, San Diego), chapter 24; and Gyllenstein, in *PCR Technology,* 1989 (Erlich, ed., Stockton Press, New York), chapter 5; each incorporated herein by reference. Typically, sequencing is carried out using one of the automated DNA sequencers which are commercially available from, for example, PE Biosystems (Foster City, Calif.), Pharmacia (Piscataway, N.J.), Genomyx Corp. (Foster City, Calif. ), LI-COR Biotech (Lincoln, Nebr.), GeneSys technologies (Sauk City, Wis. ), and Visable Genetics, Inc. (Toronto, Canada).

The nucleotide at position 937 can be identified using amplification-based genotyping methods. A number of nucleic acid amplification methods have been described which can be used in assays capable of detecting single base changes in a target nucleic acid. A preferred method is the polymerase chain reaction (PCR), which is now well known in the art, and described in U.S. Pat. Nos. 4,683,195; 4,683,202; and 4,965,188; each incorporated herein by reference. Examples of the numerous articles published describing methods and applications of PCR are found in *PCR Applications,* 1999, (Innis et al., eds., Academic Press, San Diego); *PCR Strategies,* 1995, (Innis et al., eds., Academic Press, San Diego); *PCR Protocols,* 1990, (Innis et al., eds., Academic Press, San Diego); and *PCR Technology,* 1989, (Erlich, ed., Stockton Press, New York); each incorporated herein by reference. Commercial vendors, such as PE Biosystems (Foster City, Calif.) market PCR reagents and publish PCR protocols.

Other suitable amplification methods include the ligase chain reaction (Wu and Wallace 1988, *Genomics* 4:560-569); the strand displacement assay (Walker et al., 1992, *Proc. Natl. Acad. Sci. USA* 89:392-396, Walker et al. 1992, *Nucleic Acids Res.* 20:1691-1696, and U.S. Pat. No. 5,455,166); and several transcription-based amplification systems, including the methods described in U.S. Pat. Nos. 5,437,990; 5,409,818; and 5,399,491; the transcription amplification system (TAS) (Kwoh et al., 1989, *Proc. Natl. Acad. Sci. USA* 86:1173-1177); and self-sustained sequence replication (3SR) (Guatelli et al., 1990, *Proc. Natl. Acad. Sci. USA* 87:1874-1878 and WO 92/08800); each incorporated herein by reference. Alternatively, methods that amplify the probe to detectable levels can be used, such as Qβ-replicase amplification (Kramer and Lizardi, 1989, *Nature* 339:401-402, and Lomeli et al., 1989, *Clin. Chem.* 35:1826-1831, both of which are incorporated herein by reference). A review of known amplification methods is provided in Abramson and Myers, 1993, *Current Opinion in Biotechnology* 4:41-47, incorporated herein by reference.

The nucleotide at position 937 can be identified using sequence-specific amplification or primer extension methods, which are based on the inhibitory effect of a terminal primer mismatch on the ability of a DNA polymerase to extend the primer. To detect a sequence using an sequence-specific amplification- or extension-based method, a primer complementary to the NS5A gene is chosen such that the 3' terminal nucleotide hybridizes at the substitution position. In the presence of the specific variant to be identified, the primer matches the target sequence at the 3' terminus and primer is extended. In the absence of the specific variant, the primer has a 3' mismatch relative to the target sequence and primer extension is either eliminated or significantly reduced. Allele-specific amplification- or extension-based methods are described in, for example, U.S. Pat. Nos. 5,137,806; 5,595,890; 5,639,611; and U.S. Pat. No. 4,851,331, each incorporated herein by reference. Using sequence-specific amplification-based genotyping, identification of the substitution requires only detection of the presence or absence of amplified target sequences. Methods for the detection of amplified target sequences are well known in the art. For example, gel electrophoresis (see Sambrook et al., 1989, supra.) and the probe hybridization assays described above have been used widely to detect the presence of nucleic acids.

An alternative probe-less method, referred to herein as a kinetic-PCR method, in which the generation of amplified nucleic acid is detected by monitoring the increase in the total amount of double-stranded DNA in the reaction mixture, is described in Higuchi et al., 1992, *Bio/Technology* 10:413-417; Higuchi et al., 1993, *Bio/Technology* 11: 1026-1030; Higuchi and Watson, in PCR Applications, supra, Chapter 16; U.S. Pat. No. 5,994,056; and European Patent Publication Nos. 487,218 and 512,334, each incorporated herein by reference. The detection of double-stranded target DNA relies on the increased fluorescence that ethidium bromide (EtBr) and other DNA-binding dyes exhibit when bound to double-stranded DNA. The increase of double-stranded DNA resulting from the synthesis of target sequences results in an increase in the amount of dye bound to double-stranded DNA and a concomitant detectable increase in fluorescence. For genotyping using the kinetic-PCR methods, amplification reactions are carried out using a pair of primers specific for one of the alleles, such that each amplification can indicate the presence of a particular allele. By carrying out two amplifications, one using primers specific for G at position 937 and one using primers specific for A at position 937, the genotype of the sample can be determined.

The nucleotide at position 937 can be identified using probe-based methods, which rely on the difference in stability of hybridization duplexes formed between the probe and the nucleotide variants, which differ in the degree of complementarity. Under sufficiently stringent hybridization conditions, stable duplexes are formed only between the probe and the exactly matching target sequence. The presence of stable hybridization duplexes can be detected by any of a number of well known methods. In general, it is preferable to amplify the nucleic acid prior to hybridization in order to facilitate detection. However, this is not necessary if sufficient nucleic acid can be obtained without amplification.

In some embodiments, the nucleotide present at the position 937 is identified by hybridization under sequence-specific hybridization conditions with an oligonucleotide probe exactly complementary to the region of the NS5A gene that includes position 937. The probe hybridizing sequence and sequence-specific hybridization conditions are selected such that a single mismatch at the substitution site destabilizes the hybridization duplex sufficiently so that it is effectively not formed. Thus, under sequence-specific hybridization conditions, stable duplexes will form only between the probe and the exactly complementary sequence. Thus, oligonucleotides from 14 to 60 nucleotides in length, preferably from 14 to 35 nucleotides in length, which are exactly complementary to the region of the NS5A gene that includes position 937 are within the scope of the invention.

In other embodiments, the nucleotide present at position 937 is identified by hybridization under sufficiently stringent hybridization conditions with an oligonucleotide essentially complementary to the region of the NS5A gene that includes position 937. In this embodiment, the hybridization conditions are relaxed sufficiently to allow the formation of stable duplexes with the target sequence, while maintaining sufficient stringency to preclude the formation of stable duplexes with non-target sequences. Thus, oligonucleotides from 14 to 60 nucleotides in length, preferably from 14 to 35 nucleotides in length, which are essentially complementary to the region of the NS5A gene that includes position 937, are within the scope of the invention.

The use of essentially, rather than exactly, complementary oligonucleotides may be desirable in assay formats in which optimization of hybridization conditions is limited. For example, in a typical multi-target immobilized-probe assay format, probes for each target are immobilized on a single solid support. Hybridizations are carried out simultaneously by contacting the solid support with a solution containing target DNA. As all hybridizations are carried out under identical conditions, the hybridization conditions cannot be separately optimized for each probe. The incorporation of mismatches into a probe can be used to adjust duplex stability when the assay format precludes adjusting the hybridization conditions. The effect of a particular introduced mismatch on duplex stability is well known, and the duplex stability can be routinely both estimated and empirically determined, as described above.

An oligonucleotide suitable for use in the probe-based methods of the present invention, which contains a hybridizing region either essentially complementary or exactly complementary to a target region of SEQ ID NO: 1 or to the complement of SEQ ID NO: 1, wherein the target region includes position 937, can be selected using the guidance provided herein and well known in the art. Similarly, suitable hybridization conditions, which depend on the exact size and sequence of the probe, can be selected empirically using the guidance provided herein and well known in the art. The use of oligonucleotide probes to detect single base pair differences in sequence is described in, for example, Conner et al., 1983, *Proc. Natl. Acad. Sci. USA* 80:278-282, and U.S. Pat. Nos. 5,468,613 and 5,604,099, each incorporated herein by reference.

The proportional change in stability between a perfectly matched and a single-base mismatched hybridization duplex depends on the length of the hybridized oligonucleotides. Duplexes formed with shorter probes sequences are destabilized proportionally more by the presence of a mismatch. In practice, oligonucleotides between 14 and 35 nucleotides in length are preferred for sequence-specific detection.

Furthermore, because the ends of a hybridized oligonucleotide undergo continuous random dissociation and re-annealing due to thermal energy, a mismatch at either end destabilizes the hybridization duplex less than a mismatch occurring internally. Preferably, for discrimination of a single base pair change in target sequence, the probe sequence is selected which hybridizes to the target sequence such that the nucleotide substitution site occurs in the interior region of the probe.

The above criteria for selecting a probe sequence which hybridizes to SEQ ID NO: 1 apply to the hybridizing region of the probe, i.e., that part of the probe which is involved in hybridization with the target sequence. A probe may be bound to an additional nucleic acid sequence, such as a poly-T tail used to immobilize the probe, without significantly altering the hybridization characteristics of the probe. One of skill in the art will recognize that for use in the present methods, a probe bound to an additional nucleic acid sequence which is not complementary to the target sequence and, thus, is not involved in the hybridization, is essentially equivalent to the unbound probe. In preferred embodiments of the probe-based methods for determining the NS5A genotype, a nucleic acid sequence from the NS5A gene which encompasses the substitution site is amplified and hybridized to the probes under sufficiently stringent hybridization conditions. The nucleotide sequence is inferred from the pattern of binding of the probes to the amplified target sequence. In this embodiment, amplification is carried out in order to provide sufficient nucleic acid for analysis by probe hybridization. Thus, primers are designed such that a region of the NS5A gene encompassing the substitution site is amplified regardless of which nucleotide is present in the sample. Sequence-independent amplification is achieved using primers which hybridize to conserved regions of the NS5A gene.

Suitable assay formats for detecting hybrids formed between probes and target nucleic acid sequences in a sample are known in the art and include the immobilized target format and immobilized probe assay formats. These assay formats are described in U.S. Pat. Nos. 5,310,893; 5,451,512; 5,468,613; and 5,604,099; each incorporated herein by reference. In addition, the microchip or microarray technologies are also applicable to the probe-based detection method of the present invention. Essentially, in microchips, a large number of different oligonucleotide probes are immobilized in an array on a substrate or carrier, e.g. a silicon chip or glass slide. Target nucleic acid sequences to be analyzed can be contacted with the immobilized oligonucleotide probes on the microchip (Lipshutz et al., 1995, *Biotechniques*, 19:442-445). Alternatively, the multiple target nucleic acid sequences to be studied are fixed onto a substrate an an array of probes is contacted with the immobilized target sequences (Drmanac et al., 1998, *Nature Biotechnology*, 16:54-58). Numerous microchip technologies have been developed incorporating one or more of the above described techniques for detecting single nucleotide mutations. The microchip technologies, combined with computerized analysis tools allow fast screening in a large scale. The adaptation of the microchip technologies to the present invention will be apparent to a person of skill in the art appraised of the present disclosure (Wilgenbus et al., 1999, *J. Mol. Med.*, 77:761-786).

A preferred probe-based genotyping technique to detect the nucleotide substitutions in the present invention is the "5' nuclease reaction", embodiments of which are described in U.S. Pat. Nos. 5,210,015; 5,487,972; and 5,804,375; and Holland et al., 1988, *Proc. Natl. Acad. Sci. USA* 88:7276-7280, each incorporated herein by reference. Reagents and instruments used to carry out the 5' nuclease reaction such as the COBAS TAQMAN™ system from Roche Diagnostics are familiar to those of skill in the art.

Briefly, in a 5' nuclease reaction, a nucleic acid is contacted with a primer and a probe under conditions in which the primer and probe hybridize to a strand of the nucleic acid. The nucleic acid, primer and probe are also contacted with a nucleic acid polymerase having 5' to 3' nuclease activity. Nucleic acid polymerases possessing 5' to 3' nuclease activity can cleave the probe hybridized to the nucleic acid downstream of the primer. The 3' end of the primer provides the initial binding site for the nucleic acid polymerase. As soon as the bound polymerase encounters the 5' end of the probe, the polymerase can cleave fragments from the probe.

The primer and probe can be designed such that they anneal in close proximity on the nucleic acid such that binding of the nucleic acid polymerase to the 3' end of the primer automatically puts it in contact with the 5' end of the probe. In this process, polymerization is not required to bring the nucleic acid polymerase into position to accomplish the cleavage. The term "polymerization-independent cleavage" refers to this process.

Alternatively, if the primer and probe anneal to more distantly spaced regions of the nucleic acid, polymerization must occur before the nucleic acid polymerase encounters the 5' end of the probe. As the polymerization continues, the polymerase progressively cleaves fragments from the 5' end of the probe. This cleaving continues until the remainder of the probe has been destabilized to the extent that it dissociates from the template molecule. The term "polymerization-dependent cleavage" refers to this process.

One advantage of polymerization-independent cleavage lies in the elimination of the need for amplification of the nucleic acid. In the absence of primer extension, the strand of the nucleic acid is substantially single-stranded. Provided the primer and probe are adjacently bound to the nucleic acid, sequential rounds of oligonucleotide annealing and cleavage of fragments can occur. Thus, a sufficient amount of fragments can be generated, making detection possible in the absence of polymerization.

In either process, a sample is provided which contains the nucleic acid. The nucleic acid contained in the sample may be first reverse transcribed into cDNA, if necessary, and then denatured, using any suitable denaturing method, including physical, chemical, or enzymatic means, which are known to those of skill in the art. A preferred physical means for strand separation involves heating the nucleic acid until it is completely (>99%) denatured. Typical heat denaturation involves temperatures ranging from about 80° C. to about 105° C., for times ranging from about 1 to 10 minutes. As an alternative to denaturation, the nucleic acid may exist in a single-stranded form in the sample, such as, for example, single stranded RNA or DNA viruses.

The denatured nucleic acid strand is then incubated with a primer and a probe under hybridization conditions, conditions which enable the binding of the primer and probe to the nucleic acid strand. In some embodiments, two primers can be used to amplify the nucleic acid. As known in the art, the two primers are selected so that their relative positions along the nucleic acid are such that an extension product synthesized from one primer, when the extension produce is separated from its template (complement), serves as a template for the extension of the other primer to yield a replicate chain of defined length.

Because the complementary strands are typically longer than either the probe or primer, the strands have more points of contact and thus a greater chance of finding each other over any given period of time. A high molar excess of probe, plus the primer, helps tip the balance toward primer and probe annealing rather than template reannealing.

The primer must be sufficiently long to prime the synthesis of extension products in the presence of the agent for polymerization. The exact length and composition of the primer will depend on many factors, including temperature of the annealing reaction, source and composition of the primer, proximity of the probe annealing site to the primer annealing site, and ratio of primer:probe concentration. For example, depending on the complexity of the sequence, the oligonucleotide primer typically contains about 15-30 nucleotides, although it may contain more or fewer nucleotides. The primers must be sufficiently complementary to selectively anneal to their respective strands and form stable duplexes.

Each primer can be selected to be "substantially" complementary to a strand of the nucleic acid. The primers need not reflect the exact sequence of the template, but must be sufficiently complementary to selectively hybridize to their respective strands. Non complementary bases or longer sequences can be interspersed into the primer or located at the ends of the primer, provided the primer retains sufficient complementarity with its template strand to form a stable duplex therewith. The non-complementary nucleotide sequences of the primers may include restriction enzyme sites.

To enhance the likelihood that the probe will have annealed to its complementary nucleic acid before primer extension polymerization reaches this duplex region, or before the polymerase attaches to the upstream oligonucleotide in the polymerization-independent process, a variety of techniques may be employed. Short primer molecules generally require cooler temperature to form sufficiently stable hybrid complexes with the nucleic acid. Therefore, the probe can be designed to be longer than the primer so that the probe anneals preferentially to the nucleic acid at higher temperatures relative to primer annealing.

One can also use primers and probes having differential thermal stability. For example, the nucleotide composition of the probe can be chosen to have greater G/C content and, consequently, greater thermal stability than the primer. Or for example, non-conventional DNA bases may be incorporated into primers or probes to result in either greater or lesser thermal stability in comparison to primers or probes having only conventional DNA bases. The thermocycling parameters can also be varied to take advantage of the differential thermal stability of the probe and primer. For example, following the denaturation step in thermocycling, an intermediate temperature may be introduced which is permissible for probe binding but not primer binding, and then the temperature is further reduced to permit primer annealing and extension.

To preferentially favor binding of the probe before the primer, a high molar excess of probe to primer concentration can also be used. Such probe concentrations are typically in the range of about 2 to 20 times higher than the respective primer concentration, which is generally $0.5-5 \times 10^{-7}$ M.

The primers and probe may be prepared by any suitable method. Methods for preparing oligonucleotides of specific sequence are known in the art, and include, for example, cloning and restriction of appropriate sequences, and direct chemical synthesis. Chemical synthesis methods may include, for example, the phosphotriester method described by Narang et al., 1979, *Methods in Enzymology* 68:90, the phosphodiester method disclosed by Brown et al., 1979, *Methods in Enzymology* 68:109, the diethylphosphoramidate method disclosed in Beaucage et al., 1981, *Tetrahedron Letters* 22:1859, and the solid support method disclosed in U.S. Pat. No. 4,458,066. In addition, modifications may be incorporated into oligonucleotides to impact enzyme behavior with respect to the oligonucleotides. For example, incorporation of modified phosphodiester linkages (e.g., phopshorothioate, methylphosphonates, phosphoamidate, or boranophosphate) or linkages other than a phosphorous acid derivative into a probe may be used to prevent cleavage at a selected site; or, for example, the inclusion of 2'-amino modified sugars will likely favor displacement over digestion of the oligonucleotide.

Template-dependent extension of the oligonucleotide primer(s) is catalyzed by a polymerizing agent in the presence of adequate amounts of the four deoxyribonucleoside triphosphates (dATP, dGTP, dCTP, and dTTP) or analogs as discussed above, in a reaction medium which is comprised of the appropriate salts, metal cations, and pH buffering system. Suitable polymerizing agents are enzymes known to catalyze primer and template-dependent DNA synthesis and possess the 5' to 3' nuclease activity. Known DNA polymerases include, for example, *E. coli* DNA polymerase I, Tth DNA polymerase, *Bacillus stearothermophilus* DNA polymerase, *Thermococcus littoralis* DNA polymerase, Taq DNA polymerase, and Z05 DNA polymerase. The reaction conditions for catalyzing DNA synthesis with these DNA polymerases are well known in the art. To be useful in the present invention, the polymerizing agent must efficiently cleave the oligonucleotide and release labeled fragments so that the signal is directly or indirectly generated.

The products of the synthesis are duplex molecules consisting of the template strands and the primer extension strands. Byproducts of this synthesis are probe fragments which can consist of a mixture of mono-, di- and larger nucleotide fragments. Repeated cycles of denaturation, probe and primer annealing, and primer extension and cleavage of the probe result in the exponential accumulation of the region defined by the primers and the exponential generation of labeled fragments. Sufficient cycles are run to achieve a detectable amount of probe fragments, which is generally several orders of magnitude greater than background signal.

In a preferred method, the PCR reaction is carried out as an automated process which utilizes a thermostable enzyme. In this process the reaction mixture is cycled through a denaturing step, a probe and primer annealing step, and a synthesis step, whereby cleavage and displacement occur simultaneously with primer dependent template extension. A thermal cycler, such as the commercially available machine from Applied Biosystems, which is specifically designed for use with a thermostable enzyme, may be employed.

Temperature stable polymerases are preferred in this automated process because the preferred way of denaturing the double stranded extension products is by exposing them to a high temperature (about 95° C.) during the PCR cycle. For example, U.S. Pat. No. 4,889,818 discloses a representative thermostable enzyme isolated from *Thermus aquaticus*. Additional representative temperature stable polymerases include, e.g., polymerases extracted from the thermostable bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima, Thermococcus littoralis*, and *Methanothermus fervidus*.

The probe in a 5' nuclease reaction is any oligonucleotide that can be used to identify the genotype of the target nucleic acid. Typically, the probe comprises a nucleotide sequence that corresponds to a region in the target nucleic acid. To practise the methods of the present invention, the region should comprise position 937 of the NS5A gene.

The probe nucleotide sequence can be of any length sufficient to generate fragments in the nuclease reactions. In certain embodiments, probe nucleotide sequence can be comprised of at least 6 nucleotides in length and usually fewer than 140 nucleotides. In one embodiment, the probe will be between 14 and 60 nucleotides in length. In a preferred embodiment, the probe will be between 14 and 35 nucleotides in length. The length of the probe will be chosen to give sufficient thermodynamic stability to ensure hybridization of the probe to its target at the temperature of the annealing step of PCR. For example, probes with non-conventional DNA bases may be longer or shorter than those with conventional DNA bases. As another example, probes with A/T-rich sequences will be longer than those with G/C-rich sequences. The site of the nucleotide variation can be at any location within the probe nucleotide sequence. In preferred embodiments, the site of the nucleotide variation is not at the 5' end of the probe nucleotide sequence.

Typically, the probe nucleotide sequence is identical or complementary to the target region. However, the probe nucleotide sequence can have less than 100% identity or complementarity to the target nucleotide region. In certain embodiments of the invention, the probe nucleotide sequence can have 99%, 98%, 97%, 96%, 95%, 90%, 85% or 80% complementarity or identity to the target nucleotide region. In certain embodiments of the invention, the probe nucleotide sequence hybridizes to the target nucleotide region under stringent conditions. In other embodiments of the invention, the probe nucleotide sequence hybridizes to the target nucleotide region under low stringency conditions.

In addition to the probe nucleotide sequence, the probe can comprise additional nucleotide sequences or other moieties that do not interfere with methods of the instant invention. In convenient embodiments of the invention, the probe can comprise additional nucleotide sequences or other moieties that facilitate the methods of the instant invention. For instance, the probe can be blocked at its 3' terminus to prevent undesired amplification priming. Also, moieties may be present within the probe that destabilize hybridization of the probe or probe fragments with the target nucleotide sequence.

In certain embodiments of the invention, the probe can comprise a label. In convenient embodiments, the label can be a label that facilitates the determination of the sizes of the fragments of the target probe produced by the nuclease reactions.

The probe can be labeled by incorporating moieties detectable by spectroscopic, photochemical, biochemical, immunochemical, or chemical means. The method of linking or conjugating the label to the oligonucleotide probe depends, of course, on the type of label(s) used and the position of the label on the probe.

A variety of labels which would be appropriate for use in the assay, as well as methods for their inclusion in the probe, are known in the art and include, but are not limited to, enzymes (e.g., alkaline phosphatase and horseradish peroxidase) and enzyme substrates, radioactive atoms, fluorescent dyes, chromophores, chemiluminescent labels, electrochemiluminescent labels, such as Origin™ (Igen), ligands having specific binding partners, or any other labels that may interact with each other to enhance, alter, or diminish a signal. Of course, should the nuclease reactions be practiced using a Thermo Cycler instrument, the label should be able to survive the temperature cycling required in this automated process.

Among radioactive atoms, $^{32}P$ is preferred. Methods for introducing $^{32}P$ into nucleic acids are known in the art, and include, for example, 5' labeling with a kinase, or random insertion by nick translation. Enzymes can typically detected by their activity. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $^{125}I$ may serve as a radioactive label or as an electron-dense reagent. HRP may serve as enzyme or as antigen for a monoclonal antibody. Further, one may combine various labels for desired effect. For example, one might label a probe with biotin, and detect its presence with avidin labeled with $^{125}I$, or with an anti-biotin monoclonal antibody labeled with HRP. Other permutations and possibilities will be readily apparent to those of ordinary skill in the art, and are considered as equivalents within the scope of the instant invention.

The labels may be attached to the oligonucleotide directly or indirectly by a variety of techniques. Depending on the precise type of label used, the label might be located at the 5' or 3' end of the probe, located internally in the probe's nucleotide sequence, or attached to spacer arms of various sizes and compositions to facilitate signal interactions. Using commercially available phosphoramidite reagents, one can produce oligomers containing functional groups (e.g., thiols or primary amines) at either terminus via an appropriately protected phosphoramidite, and can label them using protocols described in, for example, *PCR Protocols: A Guide to Methods and Applications*, ed. by Innis et al., Academic Press, Inc., 1990.

Methods for introducing oligonucleotide functionalizing reagents to introduce one or more sulfhydryl, amino or hydroxyl moieties into the oligonucleotide probe sequence, typically at the 5' terminus are described in U.S. Pat. No. 4,914,210. A 5' phosphate group can be introduced as a radioisotope by using polynucleotide kinase and [gamma-$^{32}P$]ATP to provide a reporter group. Biotin can be added to the 5' end by reacting an aminothymidine residue or alkylamino linker, introduced during synthesis, with an N-hydroxysuccinimide ester of biotin.

Labels at the 3' terminus may employ polynucleotide terminal transferase to add the desired moiety, such as for example, cordycepin $^{35}S$-dATP, and biotinylated dUTP.

Oligonucleotide derivatives are also available labels. For example, etheno-dA and etheno-A are known fluorescent adenine nucleotides which can be incorporated into an oligonucleotide probe. Similarly, etheno-dC is another analog that could be used in probe synthesis. The probes containing such nucleotide derivatives may be hydrolyzed to release much more strongly fluorescent mononucleotides by the polymerase's 5' to 3' nuclease activity as DNA polymerase extends a primer during PCR.

In a preferred embodiment to practise the present invention, the label is fluorescent to facilitate the detection of oligonucleotide fragments. Labels include, but are not limited to, fluorescein, polyhalofluoresceins preferably hexachlorofluorescein, coumarins, rhodamines, cyanines, oxazines, thiazines, and squaraines. In a further preferred embodiment, a single probe is dual-labeled with a fluorescent dye (i.e., a label) and a quencher. When the probe is intact, the fluorescence of the label is quenched by the quencher. Cleaving the probe between the label and quencher results in less quenching of the label's emitted fluorescence. An exemplary combination to practise this aspect of the invention is the fluorescent dye rhodamine 590 and the quencher crystal violet.

The identity of the nucleotide at position 937 of the NS5A gene may be determined in the same assay with the determination of the type or subtype of the HCV in a sample (i.e. HCV genotyping assay) using a single 5' nuclease reaction. In such an embodiment, a probe that is used to detect the nucleotide substitutions at position 937 in the NS5A gene is mixed with one or more probes that are used for HCV genotyping assays (for example probes that hybridize in the 5'UTR region of the HCV genome where there is high sequence diversity) inside a single 5' nuclease reaction. In a preferred embodiment, each individual probe will comprise its own unique label (for example a unique fluorescent dye) to distinguish its signal from the signal(s) generated from the other probes inside the single 5' nuclease reaction.

The nucleotide at position 937 can be identified using a derivation of the 5' nuclease reaction called post-PCR melting/annealing analysis. Dual-labeled probes (i.e. probes comprising a fluorescent dye with a quencher) in 5' nuclease reactions have typically been used to generate fluorescent signal during real-time or kinetic PCR, in the form of a growth curve, from which a Ct is calculated and used to generate results in either a quantitative or qualitative algorithm. During this process, the probe is cleaved by an enzyme with 5' nuclease activity, generating a variety of DNA fragments, some of which are still labeled with the fluorescent reporter. Once these fragments are generated, they can no longer participate in signal generation. However, under some circumstances, full-length intact dual-labeled probe can be left behind after the PCR is complete. If there is sufficient probe left, it can be used to provide further information about the target nucleic acid that has been amplified, by performing a melting step, during which the probe is melted off the target nucleic acid, and the resulting change in fluorescence used to determine the melting temperature (Tm) of the probe to that particular target nucleic acid, which can be correlated with sequence matches and mismatches (i.e. genotyping). The change in fluorescence is due to the shift in the distance between the fluorescent reporter and the quencher as the probe transitions between a random coil structure and an annealed structure, based-paired with the target nucleic acid. By performing asymmetric PCR whereby the concentration of the primer which generates the strand to which the probe binds is in excess, it would reduce the amount of probe cleaved during PCR and ensures that sufficient probe is left behind to perform the post-PCR melting analysis.

The nucleotide at position 937 can be determined by the use of hindered intercalating compounds or agents as described in U.S. Pat. No. 6,031,098, hereby incorporated by reference in its entirety. Briefly, these compounds which can bear a detectable label or are capable of catalyzing photolysis are sufficiently hindered such that they intercalate only between nucleotide bases in the presence of a base mismatch, and are useful for detecting single nucleotide variations.

Another useful technique in detecting the nucleotide at position 937 is mass spectrometry (MS). The most commonly used MS technology in the area of nucleic acid genotyping has been Matrix Assisted Laser Desorption Ionization (MALDI-MS) although Liquid Chromatography coupled to Electrospray/Ionspray (LC-ESI/MS) is also gaining as an important tool. Typically, determination of nucleic acid sequence by MS is done through conventional DNA sequencing methods such as the chain termination method using a primer along with a defined mixture of deoxyribonucleotides and dideoxyribonucleotides and the measurement of the resulting "ladder" by MALDI. In another method described in U.S. Pat. No. 6,258,538, hereby incorporated by reference in its entirety, the target nucleic acid is immobilized to a solid support. A primer is then annealed to the target nucleic acid at a site adjacent to nucleotide position to be analyzed. Primer extension is carried out in the presence of a selected mixture of dexoyribonucleotides and dideoxyribonucletides. The resulting mixture of extended and unextended primers is then analyzed by mass spectrometry to determine the identity of the nucleotide at the position in question.

Protein-based detection techniques may also prove to be useful, especially in determining the identity of the amino acid at position 313 of the NS5A protein of HCV-1a of the present invention. To detect amino acid variations, protein sequencing techniques may be used. For example, NS5A protein or fragment thereof can be synthesized by recombinant expression using a NS5A polynucleotide fragment isolated from an individual to be tested. Preferably, NS5A cDNA fragment of no more than 100 to 150 base pairs encompassing nucleotide position 937 is used. The amino acid sequence of the peptide can then be determined by conventional protein sequencing methods. The recently developed HPLC-microscopy tandem mass spectrometry technique may also be used for determining the amino acid sequence variations. In this technique, proteolytic digestion is performed on a protein, and the resulting peptide mixture is separated by reversed-phase chromatographic separation. Tandem mass spectrometry is then performed and the data collected therefrom is analyzed. See Gatlin et al., *Anal. Chem.,* 72:757-763 (2000).

Other useful protein-based detection techniques include immunoaffinity assays based on idiotype-specific antibodies, i.e., antibodies specific to the proteins comprising the amino acid substitutions according to the present invention. Antibodies can be used to immunoprecipitate specific proteins from solution samples or to immunoblot proteins separated by, e.g., polyacrylamide gels. Immunocytochemical methods can also be used in detecting specific protein polymorphisms in tissues or cells. Other well known antibody-based techniques can also be used including, e.g., enzyme-linked immunosorbent assay (ELISA), radioimmuno-assay (RIA), immunoradiometric assays (IRMA) and immunoenzymatic assays (IEMA), including sandwich assays using monoclonal or polyclonal antibodies. See e.g., U.S. Pat. Nos. 4,376,110 and 4,486,530, both of which are incorporated herein by reference.

The present invention also relates to kits, container units comprising useful components for practicing the present method. A useful kit can contain oligonucleotides used to detect the nucleotide substitution at position 937 in the NS5A gene substitution at position 937. In some cases, detection probes may be fixed to an appropriate support membrane. The kit can also contain amplification primers for amplifying a region of the NS5A locus encompassing the substitution site, as such primers are useful in the preferred embodiment of the invention. Alternatively, useful kits can contain a set of primers comprising a sequence-specific primer for the specific amplification of the NS5A gene. Other optional components of the kits include additional reagents used in the genotyping methods as described herein. For example, a kit additionally can contain an agent to catalyze the synthesis of primer extension products, substrate nucleoside triphosphates, means for labeling and/or detecting nucleic acid (for example, an avidin-enzyme conjugate and enzyme substrate and chromogen if the label is biotin), appropriate buffers for amplification or hybridization reactions, and instructions for carrying out the present method.

The examples of the present invention presented below are provided only for illustrative purposes and not to limit the scope of the invention. Numerous embodiments of the invention within the scope of the claims that follow the examples will be apparent to those of ordinary skill in the art from reading the foregoing text and following examples.

EXAMPLES

Overview of Roferon Clinical Study

Roferon®-A (IFN-α-2A) Trial N-139203/NV14524B was a randomized, multi-center phase III clinical study completed in July 1997. The goal was to compare the efficacy and safety of Roferon®-A (regimen from 6 MIU to 3MIU) for 24 weeks and 48 weeks in the treatment of chronic HCV patients (see Table 1).

The distribution of HCV genotypes among the patients are presented in Table 2. Based on the probability response investigated using Logistic Regression procedure in SAS, there was no discrepancy in pre-study measures (viremia, HCV genotypes, viral response, age, sex, gender, race, body surface area, stage of disease, histological activity index, and ALT).

The time windows used to collect the biochemical (liver enzyme test or ALT) and virological (viral load by PCR) measurements for data analysis are Week 0 (first day of active trial treatment), Week 12, Week 20, Week 24, Week 48 and Week 72. All analyses including tables, listings and graphics were performed using SAS PROC GLM procedure. The response rate was 15% in 24-week group and 19% in 48-week and they were statistically equivalent.

TABLE 1

Group classification

| group # | duration for received dose of 6 MIU | duration for received dose of 3 MIU | #of total patients | # of patient with missing follow-up efficacy |
|---|---|---|---|---|
| Grp 1 | 12 weeks | 12 weeks | 212 | 26 |
| Grp 2 | 12 weeks | 36 weeks | 210 | 45 |

TABLE 2

Genotype distribution

| Genotype | # in Grp1 | # in Grp2 |
|---|---|---|
| 1a | 89 | 93 |
| 1b | 55 | 55 |
| 2a-c | 29 | 33 |
| 3a-b | 30 | 23 |
| 4c | 2 | 1 |
| 6 | 0 | 1 |
| missing | 7 | 4 |

Overview of Sequence Analysis

Both biochemical (ALT) and virological (PCR) response at various time points were plotted and used to assess the treatment outcome (see Table 3 for the rules of treatment outcome classification). Using stored patient serum from a Roferon clinical trial (NV14524), pre-treatment and during-treatment sequences from patients with No Response (NR) or Complete Response (CR) in viral subgenome NS5A region were obtained from Professional Genetics Laboratories (PGL, in Uppsala, Sweden). 28 samples out of the 110 total HCV-1b patients (18 NR,10 CR) and 24 samples out of the total 182 HCV-1a patients (13NR, 11 CR) were included in the analysis. MineSet from Silicon Graphics was used to construct decision trees and to classify individuals on the basis of treatment outcome.

TABLE 3

Categories of IFN treatment outcome

| Outcome | Rules |
|---|---|
| No Response (NR) | Patients show presence of detectable HCV RNA by RT-PCR throughout treatment and at the end of treatment. |
| Breakthrough (BT) | Patients show absence of detectable HCV RNA in the serum by RT-PCR at a point during treatment followed by subsequent detection of HCV RNA during treatment followed by subsequent detectability of HCV RNA at the end of treatment. |
| Relapse Post Treatment (RPT) | Patients show absence of detectable HCV RNA in the serum by RT-PCR at the end of treatment followed by subsequent detection of HCV RNA at 24 weeks after the end of treatment. |
| Complete Response (CR) | Patients show absence of detectable HCV RNA in the serum by RT-PCR at the end of treatment and 24 weeks after the end of treatment. |

Amino acid change in the region of NS5A was converted to a binary format. Alternatively, the sequence data was represented by constructing a table of every possible amino acid for each residue position of the protein using "0" to indicate residue not present and "1" to indicate residue present to score the true amino acid sequence. The software identified mutations that were associated with either complete response or non-response to IFN treatment. From the trees, rules were constructed that described the path taken to reach the "leaves" of each branch. For example, of the 8 HCV-1b sequences possessing a valine at position 73 but not an alanine at position 195, all were non-responders. Similarly, other rules were written for all "leaves" of the tree. The usual analysis strategy for Decision Tree building is to divide the data into two parts, one for building the tree and one for testing the tree. Given the small number of patients from which NS5A sequence data was obtained, all the data was used to construct the tree. When the rules were applied back to the data, the misclassification rate was 14% for HCV-1b and 4% for HCV-1a. The results for HCV-1a in detail are given in Table 4.

TABLE 4

Assessment from NS5A-1a Prediction

| Sample | Actual Response | Amino Acid at Position 313 |
|---|---|---|
| 97-2195 | NR | I |
| 97-2227 | NR | I |
| 97-2228a | NR | I |
| 97-2228b | NR | I |
| 97-2231a | NR | I |
| 97-2231b | NR | I |
| 97-2236 | NR | V |
| 97-2481 | NR | I |
| 98-648 | NR | V |
| 98-650 | NR | I |
| 98-652a | NR | I |
| 98-652b | NR | I |

TABLE 4-continued

Assessment from NS5A-1a Prediction

| Sample | Actual Response | Amino Acid at Position 313 |
|---|---|---|
| 98-653 | NR | I |
| 97-2226 | CR | I |
| 97-2229 | CR | V |
| 97-2232 | CR | A |
| 97-2234 | CR | V |
| 97-2235 | CR | V |
| 97-2237 | CR | V |
| 98-654a | CR | V |
| 98-654b | CR | V |
| 98-656 | CR | V |
| 98-657 | CR | V |
| 98-662 | CR | V |

Thus 92% of ✓313I = NR

According to these results, the association of amino acid residue 3131 (Isoleucine) with NR was statistically significant (Fischer exact test, p<0.001) in HCV-1a patients who were 5.5 times more likely to be non-responders (resistant to interferon treatment). The observation of sequence pattern (residue 73V & 195A) in HCV-1b patients was not statistically significant (chi-squared test, $\chi^2$ with 2 degrees of freedom=1.49).

Sequence-Specific Amplification/Primer Extension

By changing the base at the 3' end of one of the primers, preferential amplification of one nucleotide variation over another can be achieved. To preferentially amplify the "A" variant, the best choice is to design an upstream primer on the sense strand, ending with A instead of G, in favor of the more destabilizing A-C mismatch over the G-T mismatch. Primer length is determined by aiming for a total Tm of approximately 65° for each primer using the *Oligonucleotide Properties Calculator* from Northwestern University, http://www.basic.northwestern.edu/biotools/oligocalc.html. The Salt Adjusted measurement is used in all cases. An example of an upstream primer is the following:

```
Sense strand:
5'- GATTCGCCCCAGCCCTGCCCA*-3'   (SEQ ID NO:3)
(asterisk denotes nucleotide position 937)
```

The matching downstream primer can be designed using Oligo Primer Analysis Software, version 6.32 (Molecular Biology Insights, Inc.). An example of such a primer is shown below:

```
Anti-sense strand:
5'- GGCCAAGGCAGTAGGTAGGGT-3'   (SEQ ID NO:4)
```

To preferentially amplify the "G" variant, one choice is to design a downstream primer on the anti-sense stand of the target DNA, ending the primer with a C instead of the T for the more destabilizing C-A mismatch. To further destabilize the mismatched terminal base, t-butyl-benzyl-dA or t-butyl-benzyl-dC, respectively, can be used for the last base, adding a bulky group which can add steric hindrance aid in the extension of the perfectly matched template over the mismatched template. An example of a downstream primer is the following:

```
Anti-sense strand:
5'- GTAGTCCGGCCGCCGCGCCCAGAC*-3'   (SEQ ID NO:5)
(asterisk denotes nucleotide position 937)
```

An example of the matching upstream primer, also using Oligo 6.32 is shown below:

```
Sense strand:
5'- CATAGGTTTGCGCCCCCTTGC-3'   (SEQ ID NO:6)
```

Amplification conditions should be as stringent as possible to favor the amplification of one variant over the other. This can be achieved by careful selection of thermal cycling conditions, especially the anneal/extension temperature to make sure that it favors amplification of the perfect 3' match over the one base-pair 3' mismatch. The primer Tm are designed around 65° C. so anneal temperatures from 58-65° C. are tested to determine the best temperature to favor the nucleotide variant of interest.

Typical thermal cycling conditions, as used on a COBAS TaqMan 96 instrument would be : 95° C. for 20 seconds followed by the 58-65° C. anneal/extend for 40 seconds for a total of 35 cycles of amplification. Following amplification, PCR products can be visualized by gel electrophoresis on 2.5% agarose gel. Additionally, the intercalating dye, Sybr Green can be added at a concentration of 0.2× during amplification for real-time PCR detection using a thermal cycler capable of reading the dye signal increase, such as the ABI PRISM 7700.

A typical PCR master mix consists of the following components, shown in final concentration per 100 µl reaction:

| | |
|---|---|
| ZO5 polymerase | 20 units |
| Tricine, pH 8.0 | 100 mM |
| KOAc, pH 7.5 | 125 mM |
| Glycerol | 9.0% |
| dATP | 200 µM |
| dUTP | 200 µM |
| dGTP | 200 µM |
| dCTP | 200 µM |
| Primer 1 | 25 pmol |
| Primer 2 | 25 pmol |
| UNG | 1 unit |

5' Nuclease Reaction

A single-base pair mismatch can be distinguished using 5' nuclease probe chemistry, and careful optimization of the anneal/extend temperature to favor cleavage of the perfectly matched template over the mismatched template. 5' Nuclease probes that contain a reporter dye (eg. FAM) and a quencher dye (eg. CY5), are usually designed with a Tm approximately 10 degrees above the Tms of the primers, to favor the probe annealing to the target sequence before primer extension, and the subsequent cleavage of the probe. This cleavage separates the reporter dye from the quencher dye, allowing the dye emissions from the reporter dye to be measured. In repeated rounds of PCR these dye emissions increase with the increasing number of amplicons generated, and can be graphed as growth curves, showing increase in fluorescence over cycle number. A mismatch between the probe and template sequence can destabilize the binding and subsequent cleavage of the probe.

An example of a 5' nuclease probe to distinguish between the "G" and "A" variants is shown below:

```
Anti-sense strand:
                                         (SEQ ID NO:7)
5'-FAM- CAGA(C/T)GGGCAGGGCTGGGGCGA-CY5-3'
```

The 5' nuclease probe is added to the PCR reaction mix as described in the previous example, at a final concentration of 10 pmol. This probe is designed to have a Tm of approximately 72° C. to bind before primers which are designed to have a Tm of approximately 65° C. Compatible primers for this probe region are also designed using the Oligo 6.32 software and examples are shown below:

```
Sense strand primer:
5'- GAGATGGGCACCATCACC-3'        (SEQ ID NO:8)

Anti-sense strand primer:
5'- GGCCAAAGTAGGGTAGGGT-3'       (SEQ ID NO:9)
```

Similar thermal cycling conditions, as mentioned in the previous example can be used.

A thermal cycler capable of exciting the reporter dye and measuring its subsequent fluorescent emission can be used, such as the COBAS TaqMan 96 or the ABI PRISM 7700.

Post-PCR Melting Analysis

Another method to distinguish between the single base pair variations is to design PCR primers that amplify the area around the variation site, and after the PCR reaction, perform melting curve generation using fluorescently-labeled probes that are designed to anneal to the region of interest. Typically, a melting curve is generated by denaturing the PCR-amplified products after the final cycle of amplification in the presence of the fluorescently-labeled probes, by heating to 95°. The temperature is then quickly cooled to 40° C. to favor rapid reannealing of probes to the homologous amplicon regions The temperature is then slowly raised to 80° C., with frequent fluorescent reads at each temperature step. A shift in the fluorescence of the labeled probes occurs when the temperature reaches the point where the probes disassociate from the amplicon, and this change in fluorescence can be measured. A single-base pair mismatch of probe to amplicon will cause the probe to disassociate or "melt" off at an earlier temperature than if it were a perfect match, allowing the differentiation of the two species by their respective melting temperatures. The PCR primer and probe assay in the 5'-nuclease example can be used to generate the melting curves.

Additionally, another type of PCR assay utilizing hybridization probe chemistry can be used to generate differential melting curves, however in this case, using two probes instead of one. The first probe, known as the "anchor" probe is designed to have a Tm at a higher temperature than the second, "sensor" probe. The anchor probe is synthesized with a 3'-terminal donor dye, such as FAM. The sensor probe is 5' terminally labeled with an acceptor dye, such as LC640. During PCR annealing, the two probes are designed to bind to the region of interest with a spacing of 1 to 5 nucleotides between the 3'-terminal end of the donor probe and the 5'-terminal end of the acceptor probe. It is during this step that the fluorescence energy is transferred from the FAM dye to the LC640 acceptor dye, and the emission of the LC640 dye is measured. For the next step of PCR, the temperature is increased to favor extension of the PCR product and disassociation of the oligo-probe pair, preserving the probes for further rounds of PCR and the subsequent generation of melting curves. A three-step PCR temperature profile can be used in this case:

95° C. denature step for 20 sec
58° C. anneal step for 20 sec
72° C. extension step for 40 secs for a total of 45 cycles This PCR must be run on an instrument capable of exciting the FAM dye and measuring the emission of the LC640 dye, such as the LightCycler 2.0.

A prophetic example of two hybridization probes that can be used as anchor and sensor to differentiate the two different NS5A variants, also utilizing the primers described in the 5' nuclease example, is as follows:

```
Anchor probe:
5'-AGTCTCGGAGATTCGCCCC-FAM3'     (SEQ ID NO:10)

Sensor probe:
5'-LC640-GCCCTGCCC(A/G)TCTG-3'   (SEQ ID NO:11)
```

The anchor probe has been designed to have a Tm of 62° C., and the sensor has been designed to have a Tm of 53° C. for a perfectly matching sensor probe to amplicon. A single base pair mismatch would most likely give a Tm at least 4° C. lower than a perfect match. The anchor probe in this case is spaced with a single base-pair between it and the sensor probe.

PCR Sequencing

The primers described in the 5' nuclease reaction example (SEQ ID NO:8 and SEQ ID NO:9) can be used for PCR sequencing using PCR conditions previously described.

What is claimed is:

1. A method for predicting response of a human subject infected with HCV-1a to interferon treatment comprising:
   a) providing an HCV-1a polynucleotide from said human subject comprising a portion that includes nucleotide position 937 of SEQ ID NO: 1, wherein SEQ ID NO: 1 represents the NS5A gene, and
   b) determining whether said nucleotide at position 937 is G or not, wherein the presence of a G at position 937 indicates an increased likelihood of sustained virologic response to interferon treatment by said human subject.

2. A method for treating a human subject infected with HCV comprising:
   a) providing an HCV-1a polynucleotide from said human subject comprising a portion that includes nucleotide position 937 of SEQ ID NO: 1, wherein SEQ ID NO: 1 represents the NS5A gene,
   b) determining whether said nucleotide at position 937 is G or not, wherein the presence of a G at position 937 indicates an increased likelihood of sustained virologic response to interferon treatment by said human subject, and
   c) if said nucleotide at position 937 is G, treating said human subject with interferon.

3. The method of claim 1 wherein the determination of the nucleotide at position 937 of SEQ ID NO: 1 further comprises the determination of the HCV strain type or subtype infecting the human subject.

4. The method of claim 1 wherein said determining step comprises performing an assay capable of detecting a single nucleotide substitution at position 937 of SEQ ID NO: 1.

5. The method of claim 4 wherein said assay comprises sequencing a portion of the NS5A gene that includes nucleotide position 937.

6. The method of claim 4 wherein said assay comprises a sequence-specific amplification or primer extension assay.

7. The method of claim 4 wherein said assay comprises a 5' nuclease reaction assay.

8. The method of claim 4 wherein said assay comprises a post-PCR melting analysis assay.

9. A method for predicting response of a human subject infected with HCV-1a to interferon treatment comprising:
   a) providing an HCV-1a polypeptide from said human subject comprising a portion that includes amino acid position 313 of the NS5A protein, and
   b) determining whether said amino acid at position 313 is Valine or not, wherein the presence of Valine at position 313 indicates an increased likelihood of sustained virologic response to interferon treatment by said human subject.

10. A method for treating a human subject infected with HCV comprising:
    a) providing an HCV-1a polypeptide from said human subject comprising a portion that includes amino acid position 313 of the NS5A protein,
    b) determining whether said amino acid at position 313 is Valine or not, wherein the presence of Valine at position 313 indicates an increased likelihood of sustained virologic response to interferon treatment by said human subject, and
    c) if said amino acid at position 313 is Valine, treating said human subject with interferon.

11. The method of claim 2 wherein the interferon treatment is selected from the group consisting of Roferon®-A (interferon alpha-2a), Pegasys® (peginterferon alpha-2a), Intron® A (interferon alpha-2b), and Peg-Intron® (peginterferon alpha-2b.

12. A method for predicting response of a human subject infected with HCV-1a to interferon treatment comprising:
    a) providing an HCV-1a polynucleotide from said human subject comprising a portion that includes nucleotide position 937 of SEQ ID NO: 1, wherein SEQ ID NO: 1 represents the NS5A gene, and
    b) determining whether said nucleotide at position 937 is A or not, wherein the presence of an A at position 937 indicates an increased likelihood of virologic non-response to interferon treatment by said human subject.

13. The method of claim 12 wherein the determination of the nucleotide at position 937 of SEQ ID NO: 1 further comprises the determination of the HCV strain type or subtype infecting the human subject.

14. The method of claim 12 wherein said determining step comprises performing an assay capable of detecting a single nucleotide substitution at position 937 of SEQ ID NO: 1.

15. The method of claim 14 wherein said assay comprises sequencing a portion of the NS5A gene that includes nucleotide position 937.

16. The method of claim 14 wherein said assay comprises a sequence-specific amplification or primer extension assay.

17. The method of claim 14 wherein said assay comprises a 5' nuclease reaction assay.

* * * * *